United States Patent [19]

Bieringer et al.

[11] Patent Number: 4,564,381

[45] Date of Patent: Jan. 14, 1986

[54] INCREASE OF CARBOHYDRATE ACCUMULATION IN PLANTS BY MEANS OF SUBSTITUTED DERIVATIVES OF PHENOXYALKANOIC ACIDS AND CYCLOHEXANEDIONES

[75] Inventors: Hermann Bieringer, Eppstein; Helmut Bürstell, Frankfurt am Main; Reinhard Handte, Hofheim am Taunus; Helmut Köcher, Hofheim am Taunus; Ernst-Friedrich Schulze, Hofheim am Taunus, all of Fed. Rep. of Germany

[73] Assignee: Hoechst Aktiengesellschaft, Frankfurt am Main, Fed. Rep. of Germany

[21] Appl. No.: 540,093

[22] Filed: Oct. 7, 1983

Related U.S. Application Data

[63] Continuation of Ser. No. 302,189, Sep. 14, 1981, abandoned.

[30] Foreign Application Priority Data

Sep. 16, 1980 [DE] Fed. Rep. of Germany ....... 3034845

[51] Int. Cl.$^4$ ...................... A01N 43/76; A01N 43/78
[52] U.S. Cl. ............................................ 71/88; 71/76; 71/90; 71/92; 71/93; 71/94; 71/95; 71/98; 71/100; 71/103; 71/105; 71/108; 71/118; 71/121; 71/124

[58] Field of Search ....................... 71/76, 88, 90, 124, 71/108

[56] References Cited

U.S. PATENT DOCUMENTS

| | | | |
|---|---|---|---|
| 3,870,501 | 3/1975 | Hirono et al. | 71/88 |
| 4,028,089 | 6/1977 | Bocion et al. | 71/88 |
| 4,130,413 | 12/1978 | Handte et al. | 71/90 |
| 4,276,080 | 6/1981 | Koerwer | 71/108 |
| 4,309,210 | 1/1982 | Quadranti et al. | 71/108 |
| 4,314,065 | 2/1982 | Serban et al. | 71/88 |
| 4,334,913 | 6/1982 | Koerwer | 71/98 |
| 4,401,459 | 8/1983 | Satomi et al. | 71/108 |
| 4,408,076 | 10/1983 | Lee | 71/108 |

OTHER PUBLICATIONS

Nickell et al., "Effects of Chemicals on Ripening, etc." (1965), Haw. Sugar Technol. 24th Ann. Conf., pp. 152-163, (1965).

*Primary Examiner*—Glennon H. Hollrah
*Assistant Examiner*—Andrew Duff Meikle
*Attorney, Agent, or Firm*—Curtis, Morris & Safford

[57] ABSTRACT

A process for increasing the carbohydrate accumulation in plants by application of compounds of the class of phenoxyphenoxy-, pyridyloxy-, benzoxazolyloxy-, benzothiazolyloxy-, quinolinyloxy-, quinazolinyloxyphenoxypropionic acid derivatives or cyclohexanedione derivatives.

5 Claims, No Drawings

INCREASE OF CARBOHYDRATE ACCUMULATION IN PLANTS BY MEANS OF SUBSTITUTED DERIVATIVES OF PHENOXYALKANOIC ACIDS AND CYCLOHEXANEDIONES

This application is a continuation of application Ser. No. 302,189, filed Sept. 14, 1981, now abandoned.

It is known that numerous compounds of the classes of aromatically or heterocyclically substituted derivatives of phenoxyalkanoic acids and cyclohexanediones have a pronounced selective activity against annual and perennial monocotyledonous plants. Several of these compounds recently have become important herbicides. Examples thereof are described in German Offenlegungsschriften Nos. 2,223,894, 2,417,487, 2,433,067, 2,531,643, 2,649,706, 2,617,804, 2,623,558, 2,628,384, 2,640,730, 2,758,002, 2,822,304, 2,914,300, 2,921,567, 2,905,458, 2,921,567, 2,830,066 and 3,004,770; published European Patent Application Nos. 0,002,246, 0,021,453, 0,003,114, 0,018,080 and 0,003,890; published Japanese Patent Application Nos. 54-122,728, 54-109,935 and 54-055,534; U.S. Pat. Nos. 4,192,669, 3,950,420, 4,011,256 and Belgian Pat. No. 875,889.

It has now been found that surprisingly a number of compounds of the above structure type cause an increased carbohydrate accumulation and thus increase of the sugar and starch content in many mono- and dicotyledonous plants when applied in subtoxic concentrations.

It is known that application of certain herbicides in low concentration shortly before the harvest increases the formation of desirable plant ingredients such as carbohydrates. This phenomenon is supposed to be the result of a transformation of the plant metabolism due to the herbicide. In the course of this process which is sometimes accompanied by a retardation of the vegetative growth, an increased accumulation of sugar, starch and other important metabolic products can occur.

Examples of products having these properties are disclosed e.g. in U.S. Pat. No. 3,556,762, German Auslegeschrift No. 2,528,867 and German Offenlegungsschrift No. 2,557,139. However, derivatives of substituted phenoxyalkanoic acids and cyclohexanediones so far have not been known for having this effect.

Subject of the present invention is therefore a process for increasing the carbohydrate content of plants, which comprises treating the plants with an effective amount of a compound of the formulae

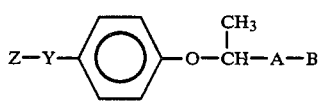

(I)

or

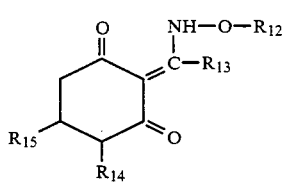

(II)

or of the salts thereof with inorganic or organic bases; the symbols in the formulae having the following meanings: Z is a radical of the formulae

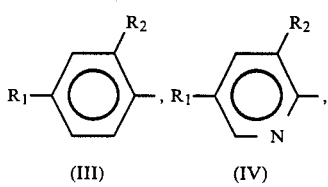

(III)            (IV)

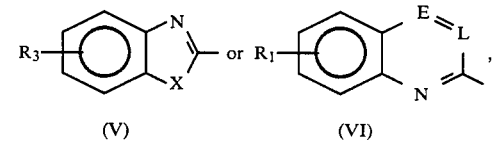

(V)            (VI)

Y is oxygen, —CH$_2$—, —N'H or —N'—(C$_1$14 C$_4$)-alkyl.

A is a direct bond or the groups —CH$_2$—CH$_2$— or —CH=CH—,

B is a radical of the formulae

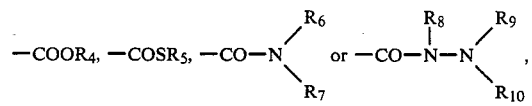

X is oxygen or sulfur,

E is CH, N, or

L is CH or N,

R$_1$ is halogen, CF$_3$, CF$_2$H, OCF$_3$, CN or NO$_2$,

R$_2$ is hydrogen, F, Cl, CF$_3$, CN or NO$_2$,

R$_3$ is hydrogen, F, Cl, Br or CF$_3$,

R$_4$ is hydrogen or an aliphatic, cycloaliphatic, aromatic or heteroaromatic radical, R$_5$ (C$_1$-C$_6$)-alkyl, (C$_3$-C$_6$)-alkenyl, benzyl, phenyl, chlorophenyl or a radical of the formula —CH(R$_8$)—COOR$_{11}$, R$_6$ is hydrogen or (C$_1$-C$_4$)-alkyl, R$_7$ is hydrogen, (C$_1$-C$_{10}$)-alkyl, phenyl optionally mono- or disubstituted by Cl and/or CH$_3$, or is a radical of the formula —CH(R$_8$)—COOR$_{11}$, R$_6$ and R$_7$ together with the nitrogen atom form a pyrrolidine, piperidine or morpholine ring, R$_8$ is hydrogen or CH$_3$, R$_9$ and R$_{10}$ each are hydrogen or (C$_1$-C$_4$)-alkyl, R$_9$ is furthermore also phenyl, R$_{11}$ is hydrogen, (C$_1$-C$_4$)-alkyl or a cation equivalent of an inorganic or organic acid, R$_{12}$ is (C$_1$-C$_4$)-alkyl, allyl or phenyl, R$_{13}$ is H, (C$_1$-C$_4$)-alkyl or phenyl, R$_{14}$ is H, (C$_1$-C$_4$)-alkoxycarbonyl or (C$_1$-C$_4$)-alkyl, R$_{15}$ is (C$_1$-C$_4$)-alkyl- or phenylthio(C$_1$-C$_3$)alkyl, (C$_1$-C$_4$)-alkyl- or phenylsulfinyl- or -sulfonyl-(C$_1$-C$_3$)-alkyl or stands for 1 or 2 (C$_1$-C$_4$)-alkyl or (C$_1$-C$_4$)-alkoxycarbonyl groups.

The compounds of formula II may occur in several tautomeric forms of which formula II denotes only one.

In the formulae, alkyl and alkenyl radicals may be linear or branched. "Halogen" stands for fluorine, chlorine or bromine. Salt-forming cations are above all alkali metal ($Na^+$, $K^+$) cations and ammonium cations, furthermore for example alkaline earth metal cation equivalents ($\frac{1}{2}$ $Ca^{++}$, $\frac{1}{2}$ $Mg^{++}$) or cations of organic ammonium bases such as $^+NH(C_2H_5)$, $^+NH_2(C_2H_5)_2$, $^+NH_3C_2H_5$, $^+N(C_2H_5)_4$, $^+NH(CH_3)_3$, $^+NH_3CH_2CH_2OH$, $^+NH_2(CH_2CH_2OH)_2$ or $^+NH(CH_2CH_2OH)_3$.

Radicals $R_4$ are in principle all those the hydroxy derivatives (ROH) of which are capable of forming esters with the free acids of compound I, such as for example: ($C_1$–$C_{12}$)-alkyl, optionally substituted by 1 to 3 halogen atoms, preferably F, Cl, Br and/or OH, ($C_1$–$C_6$)alkoxy, ($C_1$–$C_4$)alkylthio, ($C_1$–$C_6$)alkoxy-($C_2$–$C_6$)-alkoxy, halo-($C_1$–$C_2$)-alkoxy, methoxyethoxyethoxy, ($C_1$–$C_4$)alkylamino, di($C_1$–$C_4$)-alkylamino, CN, ($C_1$–$C_4$) sulfonyl or ($C_1$–$C_4$)-sulfoxyl, ($C_1$–$C_4$) alkylcarbonylamino, phenyl, oxiranyl and/or phenoxy, the latter likewise optionally mono- or disubstituted by halogen or ($C_1$–$C_4$)alkyl; ($C_5$–$C_6$)-cycloalkyl optionally substituted by halogen or $CH_3$; ($C_3$–$C_6$)-alkenyl, halo-($C_3$–$C_6$)-alkenyl; ($C_5$–$C_6$)-cycloalkenyl; ($C_3$–$C_4$)-alkinyl optionally mono- or disubstituted by ($C_1$–$C_6$)-alkyl, phenyl, halogen or ($C_1$–$C_2$)-alkoxy; phenyl optionally mono- to trisubstituted by ($C_1$–$C_4$)-alkyl, ($C_1$–$C_4$)-alkoxy, halogen, $NO_2$ or $CF_3$; furfuryl, tetrahydrofurfuryl or a radical of the formulae

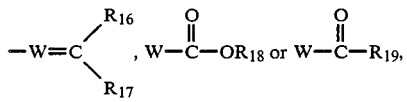

in which
$R_{16}$ is H or ($C_1$–$C_4$)-alkyl,
$R_{17}$ is H, ($C_1$–$C_4$)-alkyl, ($C_2$–$C_6$)-alkenyl, ($C_2$–$C_6$)-alkinyl or phenyl, or the two together form a pentamethylene chain,
W is ($C_1$–$C_3$)-alkylene optionally mono- or disubstituted by ($C_1$–$C_4$)-alkyl, —$COCH_3$, $COOR_{13}$,
$R_{18}$ is H, ($C_1$–$C_4$)-alkyl or a cation equivalent of an organic or inorganic base; and
$R_{19}$ is ($C_1$–$C_4$)-alkyl.

Preferred compounds of the formula I are those where B is the —$COOR_4$ group, and among these, compounds are preferred in which Y is oxygen and A a direct bond.

Especially suitable are compounds of the formula I in which $R_1$ is fluorine, chlorine, bromine or $CF_3$, and $R_2$ is hydrogen or chlorine, or in which Z is the radical of the formula V.

The compounds of the formulae I and II may be present as racemates or optical isomers. Suitable for application according to the invention are the optically inactive racemates as well as the optically active D-forms of the compounds.

Examples of compounds of the formula I are the following:
2-[4-(6-Chloro-2-benzoxazolyloxy)-phenoxy]-propionic acid-($C_1$–$C_4$)alkyl ester,
2-[4-(6-chloro-2-benzothiazolyloxy)-phenoxy]-propionic acid-($C_1$–$C_4$)alkyl ester,
2-[4-(6-fluoro-2-benzoxazolyloxy)-phenoxy]-propionic acid-($C_1$–$C_4$)alkyl ester,
2-[4-(6-trifluoromethyl-2-benzothiazolyloxy)-phenoxy]-propionic acid-($C_1$–$C_4$)alkyl ester,
2-[4-(4-trifluoromethylphenoxy)-phenoxy]-propionic acid-($C_1$–$C_4$)-alkyl ester,
2-[4-(4-trifluoromethylphenoxy)-phenoxy]-acetone oxime ester,
2-[4-(3,5-dichloro-2-pyridyloxy)-phenoxy]-propionic acid-($C_1$–$C_4$)alkyl ester.
2-[4-(5-trifluoromethyl-2-pyridyloxy)-phenoxy]-propionic acid-($C_1$–$C_4$)alkyl ester,
2-[4-(6-fluoro-2-benzothiazolyloxy)-phenoxy]-propionic acid-($C_1$–$C_4$)alkyl ester,
2-[4-(6-bromo-2-benzothiazolyloxy)-phenoxy]-propionic acid-($C_1$–$C_4$)alkyl ester,
2-[4-(6-chloro-2-quinolinoxy)-phenoxy]-propionic acid-($C_1$–$C_4$)-alkyl ester,
2-[4-(6-chloro-2-quinazolinyloxy)-phenoxy]-propionic acid-($C_1$–$C_4$)alkyl ester, or the sodium salts thereof.

Preferred compounds of the formula II are those in which
$R_{12}$ is ethyl or allyl,
$R_{13}$ is ($C_2$–$C_4$)alkyl,
$R_{14}$ is H or methoxycarbonyl, and
$R_{15}$ represents 2 ($C_1$–$C_4$)alkyl groups or one ($C_2$–$C_4$)alkylthio-($C_1$–$C_3$)alkyl group, or their alkali metal salts.

Application according to the invention of the cited compounds increases the carbohydrate content of numerous mono- and dicotyledonous plants or their fruits, for example sugar cane, sugar beets, grapes, melons, a variety of other fruits, potatoes, corn, millets (sorghum) and fodder (clover, lucerne). The result in sugar cane, sugar beets and millets is an increase of the sucrose content, in fruits and grapes, for example, an increase of the fructose content, and in other plants the starch amount is raised. The advantages so obtained are notorious and need not be explained.

Contrary to the application as herbicides, the application according to the invention for influencing carbohydrate accumulation is carried out in a later stage of plant growth, where the plant is considerably less sensitive to herbicidal influence than in the emergence stage. Therefore higher doses are tolerated without damage. Advantageously, the compounds are applied from about 1 week to 5 months before harvest, after which period of time the degree of ripeness provoked by the active substances and thus the carbohydrate content has attained a maximum. Generally, it is to be noted that the speed of growth and the vegetation period of the crop plants can vary within wide limits. Sugar cane, for example, requires from 1 to 3 years, depending on climate and habitat, until it is ripe for harvesting, and the moment of application must be varied accordingly. In the case of sugar cane, therefore, and that of sorgo, the application time is for example from 1 to 13 weeks before the harvest.

The active compounds of the formula I can be applied in the form of wettable powders, emulsifiable concentrates, sprayable solutions, dusts or granules in usual formulations in which the active substance is contained in concentrations of from 2 to 95%.

Wettable powders are formulations which are uniformly dispersible in water and which, in addition to the active compound and a diluent or inert material, also contain wetting agents, for example, polyoxethylated alkylphenols, polyoxethylated oleylamines or stearylamines, alkylsulfonates or alkylphenylsulfonates and dispersing agents, for example sodium ligninsulfonate, sodium-2,2'-dinaphthylmethane-6,6'-disulfonate, or the sodium salt of oleyl-methyl taurine.

Emulsifiable concentrates are obtained by dissolving the active compound in an organic solvent, for example, butanol, cyclohexanone, dimethyl formamide, xylene or even higher-boiling aromatics, and adding a non-ionic wetting agent, for example, a polyoxyethylated alkylphenol or a polyoxyethylated oleylamine or stearylamine.

Dusting agents are obtained by grinding the active compound with finely divided solids, for example talc, natural clays, such as kaolin, bentonite, pyrophilite or diatomaceous earth.

Granules can be manufactured either by spraying the active compound onto absorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules.

The concentration of the active compound in the commercial formulations may vary within wide limits. In wettable powders, the active compound concentration varies, for example, between about 10 and 95%, the remainder consisting of one or more of the abovementioned formulation additives. In the case of emulsifiable concentrates, the active compound concentration is about 10% to 80%. Dust formulations usually contain 5-20% of active compound. In the case of granules, the active compound content in part depends on whether the active compound is in a liquid or solid form and what granulating auxiliaries, fillers and the like are used.

The commercial concentrates are diluted prior to application in usual manner, for example by means of water in the case of wettable powders and emulsifiable concentrates. Dusts, granules and sprayable solutions are generally ready for use without further dilution with inert substances.

The necessary application concentration varies according to the external conditions such as temperature, moisture etc., and depends especially on the plant species and its development stage. In principle it must be chosen in such a manner that the active substance interferes with the natural growth process of the plant without damaging it. Depending on the plant the concentration can therefore vary within wide limits, that is, for example, from 0.005 to 10.0 kg/ha or more of active substance. In the case of broad-leaf plants which are not or only insignificantly damaged by the compounds of the formulae I and II, it is preferably in a range of from 0.1 to 5, especially 0.5 to 2, kg/ha, while in the case of monocotyledonous plants generally lower concentrations (0.01 to 1 kg/ha) are applied.

If desired, the compounds can be combined with other herbicides, insecticides and fungicides.

The following examples illustrate the invention.

FORMULATION EXAMPLES

Example A

An emulsifiable concentrate is obtained from
15 parts by weight of active substance
75 parts by weight of cyclohexanone as solvent and
10 parts by weight of oxethylated nonyl phenol (10 EO) as emulsifier.

Example B

A wettable powder which is easily dispersible in water is obtained by mixing
25 parts by weight of active substance
64 parts by weight of quartz containing kaolin as inert material
10 parts by weight of potassium lignosulfonate and
1 part by weight of sodium oleyl-methyl-taurine as wetting and dispersing agent, and grinding the mixture in a pin mill.

Example C

A dusting powder is obtained by mixing
10 parts by weight of active substance and
90 parts by weight of talc as inert material
and comminuting the mixture in a pin mill.

Example D

A granular formulation consists, for example, of about
2 to 15 parts by weight of active substance and
98 to 85 parts by weight of inert granular materials such as attapulgite, pumice and quartz sand.

BIOLOGICAL EXAMPLES

The following examples demonstrate the increase of sucrose content in accordance with the process of the invention, without however limiting its scope of application in any way.

Example I

Sugar cane plants were grown in a greenhouse at 25°-35° C. and an atmospheric moisture of 65%. Different amounts of the formulated compounds were suspended in water which contained in addition about 0.25% by weight of a surfactant (nonylphenol).

0.3 ml each of the suspensions were applied to the dewlap region of the plants by means of a syringe (10 plants per concentration). On harvest after 3 weeks, the leaves of the treated plants as well as of untreated controls were removed and the internodes analyzed in groups with respect to their sucrose content. The results are listed in Table I.

TABLE I

| Active substance | | Sugar content (%) on harvest |
|---|---|---|
| Control | | 100 |
| Comp. I | 4 mg | 182 |
|  | 2 mg | 184 |
| Comp. II | 4 mg | 160 |
|  | 2 mg | 176 |
| Comp. III | 4 mg | 177 |
|  | 2 mg | 159 |
| Comp. IV | 4 mg | 169 |
|  | 2 mg | 162 |
| Comp. V | 8 mg | 151 |
| Comp. VI | 8 mg | 154 |
|  | 4 mg | 145 |
| Comp. VII | 4 mg | 183 |
|  | 2 mg | 164 |
| Comp. VIII | 4 mg | 171 |

TABLE I-continued

| Active substance | Sugar content (%) on harvest |
|---|---|
| 2 mg | 152 |

Key to symbols:
I: (D+)-ethyl-2-[4-(6-chloro-2-benzoxazolyloxy)-phenoxy]-propanoate
II: ethyl-2-[4-(6-chloro-2-benzothiazolyloxy)-phenoxy]-propanoate
III: racemate of I
IV: propyl-2-[4-(6-chloro-2-benzoxazolyloxy)-phenoxy]-propanoate
V: ethyl-2-[4-(6-chloro-2-quinoxalinyloxy)-phenoxy]-propanoate
VI: ethyl-2-[4-(6-chloro-2-quinolinyloxy)-phenoxy]-propanoate
VII: 2-(1-ethoxyimino)butyl-5-(2-ethylthio)propyl-1,3-dioxo-cyclohexane
VIII: 2-[(1-allyloxyimino)butyl]-4-methoxycarbonyl-5,5-dimethyl-3-oxo-cyclohex-1-enol sodium salt.

Example II

As in Example I, the formulated compounds were suspended in water containing 0.25 weight % of a surfactant. 0.3 ml each of the suspensions were applied to the dewlap regions of sugar cane plants which were 18 months old at the time of application (10 plants per compound and concentration).

After 5 weeks the plants were harvested, the leaves removed and the 14 upper internodes were analyzed in groups with respect to sucrose content and purity of juice according to the so-called "press method" (T. Tanimoto, Hawaiian Planters Record 57, 133 (1964)). According to this method, the sugar content is determined polarimetrically and expressed in "pol percent cane"; this value corresponds to the percentage of sucrose in the solution assuming that sucrose is the only substance in the sugar solution which turns the plane of polarized light. The determination of pol % cane is an accepted method for evaluating the sugar content of sugar cane.

The results are listed in Table II.

TABLE II

| | Application concentration | purity of juice [%] | Sucrose content [pol % cane] |
|---|---|---|---|
| Control | 0 | 78.3 | 10.1 |
| Comp. I | 4 mg | 89.2 | 15.9 |
| | 2 mg | 90.0 | 16.2 |
| Comp. II | 4 mg | 87.8 | 15.1 |
| | 2 mg | 89.6 | 15.9 |
| Comp. III | 4 mg | 88.2 | 15.7 |
| | 2 mg | 88.1 | 15.7 |
| Comp. IV | 4 mg | 89.1 | 16.1 |
| | 2 mg | 83.3 | 12.1 |

Example III

Sugar beets were grown in pots on sandy loam in a greenhouse with addition of high nitrogen doses. At the age of 14 weeks, active substance II in a concentration of 1.25 kg/ha was applied to the plants. 5 Weeks after the treatment the plants were harvested and examined for their sugar content. The results are listed in Table III in percent as compared to the control.

TABLE III

| | Beet substance | Sugar yield |
|---|---|---|
| Control | 100 | 100 |
| Comp. II | 112 | 124.2 |

The test results demonstrate that the process of the invention causes a considerable increase of sucrose content and sucrose yield in the treated plants.

The invention has been described above with respect to certain embodiments thereof, without thereby limiting its scope. Similar effects are observed when using other compounds according to the invention.

What is claimed is:

1. A process for increasing the carbohydrate content of plants which comprises treating the plants within about 1 to 13 weeks before harvest time of said plants with an effective amount of a compound of the formula

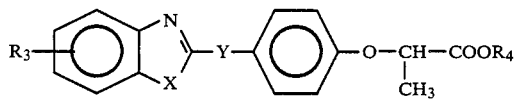

in which
Y is —O—,
X is oxygen or sulfur;
$R_3$ is H, and Cl, and
$R_4$ is ($C_1$-$C_4$)alkyl radical.

2. A process for increasing the sugar content of sugar cane, sugar beet, corn or sweet sorghum which comprises treating said plants within 1 to 13 weeks before harvest time with an effective amount of a compound of the formula

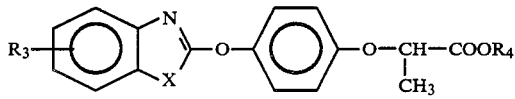

wherein X is oxygen or sulfur,
$R_3$ is Cl and $R_4$ is ($C_1$-$C_4$)alkyl.

3. The process according to claim 2, which comprises applying to said plants an active compound in the form of its optical D-isomers.

4. The process defined in claim 2 in which the compound is racemic ethyl-2-[4-(6-chloro-2-benzoxazolyloxy)-phenoxy]-propanoate.

5. The process defined in claim 2 in which the compound is racemic ethyl-2-[4-(6-chloro-2-benzothiazolyloxy)-phenoxy]-propanoate.

* * * * *